United States Patent [19]

Perlman

[11] Patent Number: 5,518,604
[45] Date of Patent: May 21, 1996

[54] BUFFER SHAPING DEVICE

[75] Inventor: Daniel Perlman, Arlington, Mass.

[73] Assignee: Brandeis University, Waltham, Mass.

[21] Appl. No.: 418,808

[22] Filed: Apr. 7, 1995

[51] Int. Cl.[6] .................... G01N 27/26; G01N 27/447
[52] U.S. Cl. .................... 204/616; 204/458; 204/466; 204/608
[58] Field of Search .................... 204/299 R, 182.8

[56] References Cited

U.S. PATENT DOCUMENTS

| | | | |
|---|---|---|---|
| 3,129,158 | 4/1964 | Raymond et al. | 204/299 R |
| 3,616,456 | 10/1971 | Valmet | 204/299 |
| 3,932,263 | 1/1976 | Brefka | 204/299 |
| 4,579,693 | 3/1986 | Kreisher et al. | 204/299 R X |
| 4,729,823 | 3/1988 | Guevara, Jr. | 204/299 R |
| 4,762,743 | 8/1988 | von Alven et al. | 204/299 R |
| 4,834,854 | 5/1989 | Sugihara et al. | 204/182.8 |
| 4,844,786 | 7/1989 | Sugihara et al. | 204/299 |
| 4,904,366 | 2/1990 | Tokita et al. | 204/299 R |
| 5,190,629 | 3/1993 | Sugihara et al. | 204/182.8 |

FOREIGN PATENT DOCUMENTS 63-210653  9/1988  Japan .................... 204/299 R

OTHER PUBLICATIONS

W. Ansorge and S. Labeit "Field Gradients Improve Resolution on DNA Sequencing Gels" Journal of Biochemical and Biophysical Methods, 10 (3–4), (1984) 237–43.

Anders Olsson et al, "Uniformly Spaced Banding Pattern in DNA Sequencing Gels by use of Field Strength Gradient" Journal of Biochemical and Biophysical Methods, 10 (1–2), (1984), 83–90.

M. D. Biggin et al. "Buffer Gradient Gels and $^{35}S$ Label as an Aid to Rapid DNA Sequence Determination" Proceeding of the National Academy of Science, USA, vol. 80 (Jul. 1983) 3963–3965.

*Primary Examiner*—John Neibling
*Assistant Examiner*—John S. Starsiak, Jr.
*Attorney, Agent, or Firm*—Lyon & Lyon

[57] ABSTRACT

Electrophoresis apparatus with a gel support configured and arranged to hold a gel, a buffer chamber configured and arranged to hold a buffer, with the buffer contacting each end of the gel, and a buffer shaper configured to be positioned near the gel support and in contact with the buffer. The buffer shaper is positioned nearer to one portion of the gel support than to another portion of the gel support to cause the depth of buffer between the gel support and the buffer shaper to vary along the length or width of the gel support and buffer shaper.

11 Claims, 2 Drawing Sheets

5,518,604

1

BUFFER SHAPING DEVICE

BACKGROUND OF THE INVENTION

This invention relates to methods and apparatus for electrophoresis of biomolecules.

It is common in the biotechnology industry and in research laboratories to electrophorese biomolecules. Such electrophoresis is performed generally within a gel matrix. The matrix is placed in electrical contact with at least two electrodes (an anode and a cathode). An electrophoresis buffer is used both within and outside of the matrix to provide electrical contact between the electrodes and the matrix. The buffer may contact not only the ends of the matrix but also may be positioned against at least one surface of the gel, e.g., against the top surface of a horizontal gel. Such gels are used, for example, in fractionation of DNA restriction fragments and PCR products, as well as in separation of other high molecular weight materials such as RNA and proteins. For example, Kreisher et al., U.S. Pat. No. 4,576,693 describes an electrophoresis apparatus and method for fabricating a gel matrix. In general, two sheets or pieces of glass or plastic are placed near to each other with spacing devices designed to create a space between the two plates. A gel matrix-forming material is then poured within the space. Buffer is contacted with the two ends of the gel matrix and material of high or low molecular weight can be electrophoresed through that matrix.

Sugihara et al., U.S. Pat. Nos. 4,834,854, 4,844,786 and 5,190,629 describe methods for forming a matrix having a concentration gradient of matrix materials along its length, having varying thicknesses along its length, or having a combination of a gradual change in thickness of matrix and change in concentration of matrix materials. Such variations in matrix materials are said to aid separation of molecules electrophoresed within the matrix.

Valmet, U.S. Pat. No. 3,616,456, describes a device for isoelectric separation of ampholytes.

Brefka, U.S. Pat. No. 3,932,263, describes an electrophoresis slide mounting means; and Firth, U.S. Pat. No. 5,232,856, describes an electroporation device.

Biggin et al., 80 *Proc. Natl. Acad. Sci. USA*, 3963, 1983, describes buffer gradient gels allegedly useful to aid in rapid DNA sequence determination.

SUMMARY OF THE INVENTION

This invention features an apparatus designed to allow the amount of buffer about a gel to be varied to allow enhanced separation of biomolecules in a matrix. By varying the buffer adjacent one side of a matrix (along the path of electrophoresis) Applicant has found a simple means to allow separation simultaneously of both high and low molecular weight materials (e.g., DNA having between 1–2 thousand bases and between 5–10 thousand bases).

Thus, in a first aspect, the invention features an electrophoresis apparatus with a gel support configured and arranged to hold a gel, a buffer chamber configured and arranged to hold a buffer with the buffer contacting each end of the gel, and a buffer shaper configured to be positioned near the gel support and in contact with the buffer. The buffer shaper is positioned nearer to one portion of the gel support than to another portion of the gel support to cause the depth of buffer between the gel support and the buffer shaper to vary along the length or width of the gel support and buffer shaper.

In preferred embodiments, the apparatus includes a gel held on or within the gel support; the buffer chamber includes an electrophoresis buffer; the buffer chamber has a buffer in contact with the gel; the buffer chamber further includes at least two electrodes; the apparatus is configured and arranged to allow an electric current to pass along the length of the gel support and through the gel; the gel support and buffer shaper are configured and arranged to provide in the buffer held therebetween, a triangular shape, a rectangular and a triangular shape, or a curved shape when the gel support and buffer shaper are viewed in longitudinal cross-section. The gel support and the buffer shaper are configured and arranged so that DNA molecules, for example, of molecular weight between about five hundred thousand and six hundred thousand Daltons can be separated (i.e., readily distinguished as two bands in the gel) on the gel without electrophoretic loss from the bottom or end of the gel of molecules of molecular weight fifty thousand Daltons.

In a second related aspect, the invention features a method for separation of electrically charged biomolecules by providing an apparatus described above, providing a gel on the gel support, and a buffer within the apparatus such that the buffer fills the area between the gel on the gel support and the buffer shaper. An electric potential is applied, and a current is generated through the buffer-filled area and the gel to cause electrophoresis of electrically charged biomolecules in the gel.

In a third related aspect, the invention features a method for forming a shaped buffer by providing an electrophoresis apparatus as described above, and providing a buffer between the buffer shaper and the gel support. The buffer is thereby shaped by the configuration of the apparatus.

In a fourth related aspect, the invention features a kit for electrophoresis including an apparatus as described above, and buffer shaper, and a buffer and materials suitable for forming a gel matrix. Such buffers and materials are well known in the art.

Other features and advantages of the invention will be apparent from the following description of the preferred embodiments thereof, and from the claims.

DESCRIPTION OF THE PREFERRED EMBODIMENTS

The drawings will first briefly be described.

Drawings FIG. 1 is a longitudinal sectional view of an electrophoresis apparatus of this invention;

STRUCTURE

Figure 1:
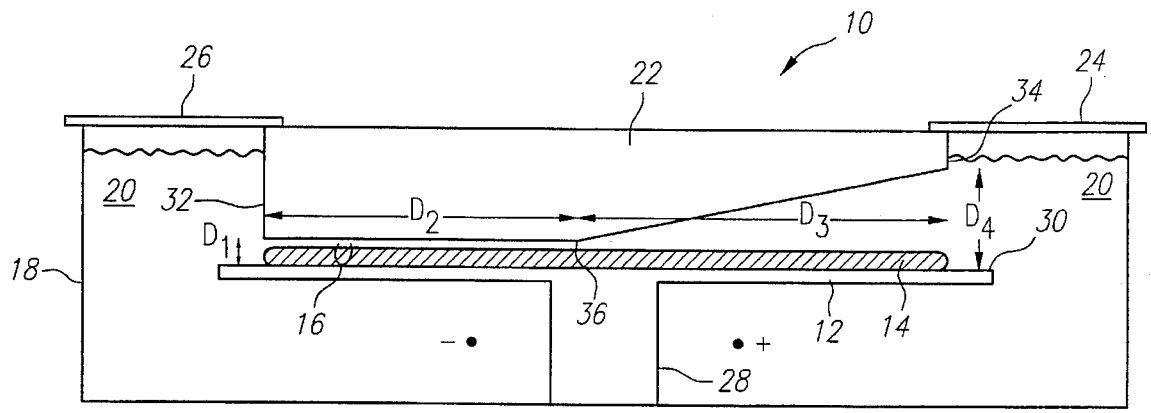

Referring to FIG. 1, a small scale or "mini-gel" electrophoresis apparatus 10 of the present invention is provided with a gel support 12 on which is placed a gel 14 having a sample well 16 into which biomolecules to be separated can be introduced. The apparatus is provided within a buffer chamber or liquid-tight box 18 containing buffer 20. Box 18 supports a buffer shaper 22 by two support elements 24, 26.

Two electrodes labelled (−) and (+) are provided on either side of a partition 28. These electrodes are in electrical contact with either end of gel matrix 14 through buffer 20. Buffer shaper 22 is provided a distance D1 (e.g., about 1–10 mm) above the upper surface 30 of gel support 12 at one end 32 of buffer shaper 22. The other end 34 of buffer shaper 22 is provided a distance D4 (e.g., about 5–20 mm) above surface 30 of gel support. The bottom of buffer shaper 22 is provided with a generally horizontal planar or rectangular shape in longitudinal sectional view from end 32 to a mid-portion 36 above surface 30 and then with a generally sloping planar or triangular shape in longitudinal sectional view from central portion 36 to end 34. Distance D2 (e.g., about 3–5 cm) between edge 32 and central portion 36 and distance D3 ((e.g., about 3–10 cm) from central portion 36 to end 34 may be the same or different. Generally it is preferred that distance D3 be equal to or up to two times the length of D2.

While FIG. 1 shows suspension of a buffer shaper above a gel, those in the art will recognize that buffer shapers can be attached in any desired manner to be suspended above a gel, or in vertical gels to be placed along side a gel matrix. Thus, those in the art will recognize that hinge or track mounting means, clamping or taping means and the like, may be used to appropriately distance the buffer shaper from the gel support and thence from a gel matrix provided on the gel support.

Figure 2:
FIGS. 2 and 3 show longitudinal views of different buffer shapers.
Figure 3:
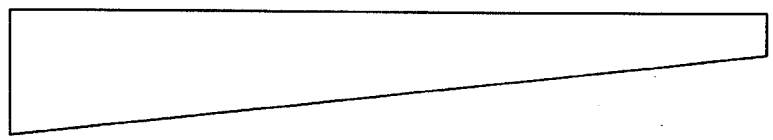

Referring to FIGS. 2 and 3, different shaped buffer shapers are shown to illustrate other embodiments of the invention. Those in the art will recognize that virtually any shape of buffer shaper may be used to advantageously effect the electrophoresis of biomolecules through a gel matrix adjacent which the buffer shaper is placed.

Figure 5:
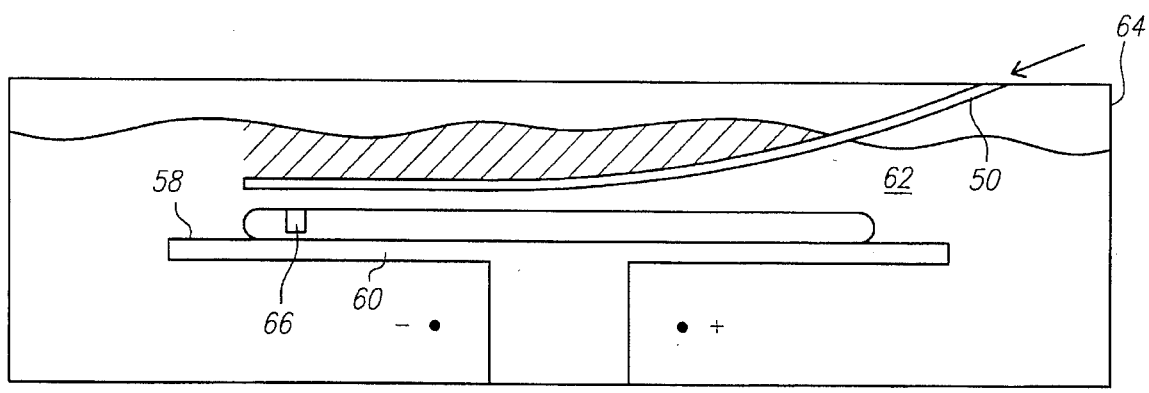
FIG. 5 is a longitudinal sectional view of an electrophoresis apparatus containing a buffer shaper sheet.
Figure 6:
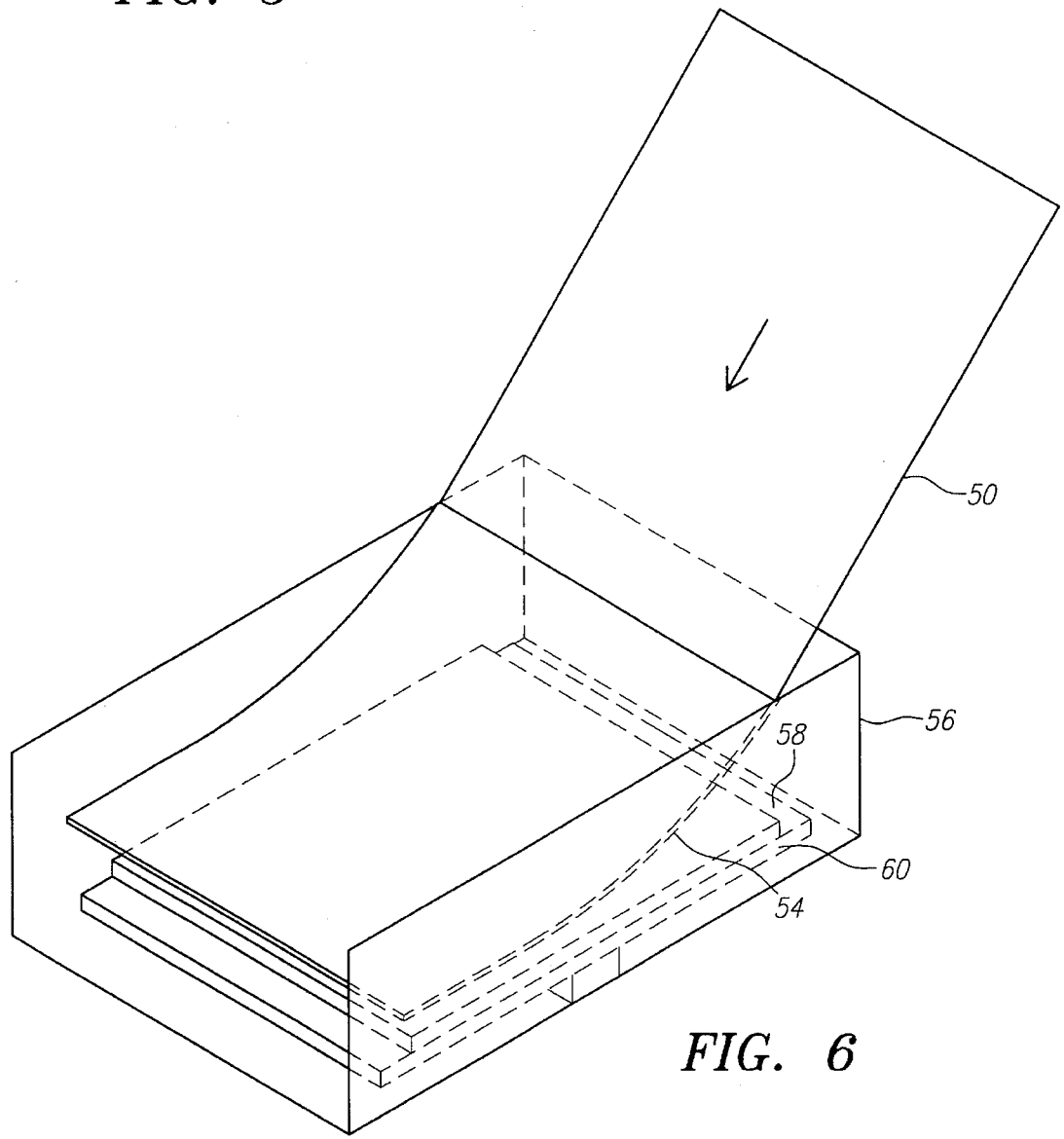
FIG. 6 is an isometric view of the apparatus shown in FIG. 5.

At least two different mechanical approaches have been used in the design and construction of buffer shapers for use in proximity to horizontal gels. The first approach shown in FIGS. 1–4 employs a space-filling three dimensional form which is generally shaped in plastic, and configured and adapted to displace a volume of buffer above the gel thereby allowing controlled variation of buffer depth over the length of the gel. Referring to FIGS. 5 and 6, other buffer shaping devices can be constructed employing a flexible sheet 50 of buffer-impermeable material such as polyolefin plastic, e.g., polymethylpentene (PMP), polypropylene, or polyethylene. Sized sheet 50 of such flexible plastic (approximately 0.005–0.050 inches thick) is configured and adapted to fit into, e.g., slide into, a symmetric pair of support grooves 52, 54 (typically in the form of a matched pair of channels) located on the inner sidewall surfaces of an electrophoresis box 56 or tank (These grooves are located on the two sidewalls running parallel to the direction of electrophoresis.) The shaped non-horizontal path of these support grooves (e.g., a linearly sloping or a curved path along the opposed inner sidewalls of the box) causes the inserted plastic sheet to assume a geometric form which may be sloped planar or non-planar depending upon the shaped path of the grooves. The height of these grooves at any point above the upper surface 58 of gel support 60 determines the depth of uninterrupted buffer which provides electrical conductivity above a gel of a given thickness. It is only this uninterrupted buffer volume which is juxtaposed to the gel (and located below the plastic buffer shaper sheet) that participates in the electrical flow of ions above and through the gel.

In practice, an electrophoretic gel is formed on, or placed on gel support 60. Buffer 62 is added to a liquid-tight box 64 and a sample of biomolecules is loaded into sample well 66. The buffer shaper sheet is slid or placed into a predetermined location using, for example, the pair of guiding support grooves on the inner sidewalls of the box 18. In a typical apparatus of the present invention, the buffer shaper sheet is inserted into the box along downward sloped grooves, from a location near the terminal end of the gel toward the sample-loading end of the gel (see FIG. 6). By inserting the buffer shaper sheet in this manner (in a direction opposite to the direction of electrophoresis) the leading edge of the sheet can be easily stopped and positioned near the sample end of the gel without mechanically disturbing the biomolecular sample (which typically has already been loaded into the sample well 66). The trailing end of the buffer shaper sheet should remain above the surface of the buffer so as to electrically isolate the volume of buffer residing above the buffer shaper sheet (see the shaded isolated area of buffer in FIG. 5). In this manner there is no flow of ionic species between the electrodes within this isolated volume of buffer and the buffer shaper sheet provides the same functionality that the buffer-displacing space-filling buffer shaper provided in FIGS. 1–4. A buffer shaper sheet fabricated from UV-transparent plastic such as PMP additionally allows UV-fluorescence gel examination of biomolecules labeled or stained with UV-fluorescent dyes such as ethidium bromide.

Method of Use

Once samples have been loaded into the gel wells, the buffer shaper is lowered into the buffer just above the gel, preferably extended past (covering) the gel wells. The buffer shaper is selected or pre-adjusted to an optimum height before loading the sample wells to avoid disturbing any samples in the wells.

Example: Dye Migration distances in gel (cm)

Figure 4:
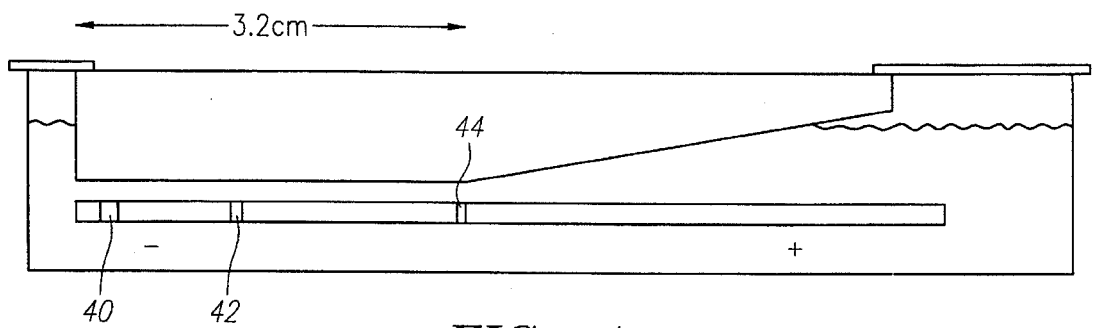
FIG. 4 is a longitudinal view of a buffer shaper and a gel showing the location of dye markers.

Referring to FIG. 4, the electrophoresis apparatus shown in FIG. 1 is reproduced in diagrammatic form for experimental evaluation of the apparatus. In this case, distance D2 is 3.2 centimeters. The buffer is standard 0.5×TPE buffer (Maniatis et al., Molecular Cloning—A Laboratory Manual, Cold Spring Harbor Laboratory, 1982) (although any standard electrophoresis buffer can be used in this experiment). A sample is provided within sample well 40 and the distance moved by Xylene cyanol 42 and Bromophenol Blue 44 is measured after various time intervals after start of electrophoresis at a constant voltage. The results are provided in the table below. These results indicate that until the Bromophenol Blue dye reaches the end of the rectangular portion of the buffer shaper and enters the triangular portion of the buffer shaper (where the depth of buffer increases above the gel in the apparatus) the ratio of movement of the two dyes is essentially constant at between 44% and 45%. However, when the Bromophenol Blue dye in the gel reaches the deeper buffer portion, this dye moves more slowly relative to its rate of movement in the shallow buffer zone reflected by the Xylene cyanol in the shallow buffer zone moving at a greater speed than the Bromophenol Blue in the deeper buffer zone. This indicates that there is a decreasing voltage gradient within the gel matrix in which the Bromophenol Blue is moving after travelling 3.2 centimeters.

| Xylene cyanol | Bromophenol Blue | Ratio |
| --- | --- | --- |
| 0.7 cm | 1.6 | 44% |
| 1.0 | 2.2 | 45% |

| Xylene cyanol | Bromophenol Blue | Ratio |
|---|---|---|
| 1.4 | 3.2 | 44% |
| 2.2 | 4.1 | 54% |
| 2.9 | 4.7 | 62% |
| 3.8 | 5.5 | 69% |

These data indicate that shaping of the buffer depth over a gel can be used to "compress" the faster-moving lower molecular weight molecules (any molecules whether they are DNA, RNA, protein or otherwise) and then allow the display and resolution of a larger range of molecular weights of molecules on a single gel. Thus, the investigator can run the gel longer and resolve the higher molecular weight upper bands while not running the lower molecular weight species off the bottom of the gel.

Other embodiments are within the following claims.

I claim:

1. Electrophoresis apparatus comprising
a gel support configured and arranged to hold a gel,
a buffer chamber configured and arranged to hold a buffer with the buffer contacting each end of the gel, and
a buffer shaper configured to be positioned near said gel support and in contact with the buffer, wherein said buffer shaper is positioned nearer to one portion of the gel support than to another portion of said gel support to cause the depth of buffer between said gel support and said buffer shaper to vary along the length or width of said gel support and buffer shaper wherein said apparatus comprises at least two electrodes, wherein said apparatus is configured and arranged to allow an electric current to pass along the length of the gel support and through the gel.

2. The electrophoresis apparatus of claim 1, said apparatus comprising a gel held on or within said gel support.

3. The electrophoresis apparatus of claim 1 wherein said buffer chamber comprises a buffer.

4. The electrophoresis apparatus of claim 2 wherein said buffer chamber comprises a buffer in contact with said gel.

5. The electrophoresis apparatus of claim 1 wherein said gel support and buffer shaper are configured and arranged to provide in the buffer held therebetween, a triangular shape, when viewed in longitudinal cross-section.

6. The electrophoresis apparatus of claim 1 wherein said gel support and said buffer shaper are configured and arranged to provide in the buffer held therebetween, a rectangular and a triangular shape when viewed in longitudinal cross-section.

7. The electrophoresis apparatus of claim 1 wherein said gel support and buffer shaper are configured and arranged to provide in the buffer held therebetween a curved shape when viewed in longitudinal cross-section.

8. The electrophoresis apparatus of claim 1 wherein said gel support and said buffer shaper are configured and arranged so that DNA molecules of molecular weight between about five hundred thousand and six hundred thousand Daltons can be separated on the gel without electrophoretic loss from the bottom or end of the gel of molecules of molecular weight fifty thousand Daltons.

9. Method for separation of molecules, comprising the steps of:
providing an electrophoresis apparatus comprising:
a gel support configured and arranged to hold a gel,
a buffer chamber configured and arranged to hold a buffer with a buffer contacting each end of the gel,
a buffer shaper configured to be positioned near said gel support and in contact with the buffer, wherein said buffer shaper is positioned nearer to one portion of the gel support than to another portion of said gel support to cause the depth of buffer between said gel support and said buffer shaper to vary along the length or width of said gel support and buffer shaper wherein said apparatus comprises at least two electrodes, wherein said apparatus is configured and arranged to allow an electric current to pass along the length of the gel support and through the gel;
providing a gel and a buffer within said apparatus such that said buffer fills the area between said gel support and said buffer shaper; and
applying an electric current through said buffer and gel to electrophorese molecules in said gel.

10. Method for forming a shaped buffer, comprising the steps of:
providing an electrophoresis apparatus, comprising:
a gel support configured and arranged to hold a gel,
a buffer chamber configured and arranged to hold a buffer with a buffer contacting each end of the gel,
a buffer shaper configured to be positioned near said gel support and in contact with the buffer, wherein said buffer shaper is positioned nearer to one portion of the gel support than to another portion of said gel support to cause the depth of buffer between said gel support and said buffer shaper to vary along the length or width of said gel support and buffer shaper wherein said apparatus comprises at least two electrodes, wherein said apparatus is configured and arranged to allow an electric current to pass along the length of the gel support and through the gel; and
providing a buffer between said buffer shaper and said gel support wherein said buffer is shaped by the configuration of said apparatus.

11. Kit for electrophoresis, comprising:
an electrophoresis apparatus, comprising:
a gel support configured and arranged to hold a gel,
a buffer chamber configured and arranged to hold a buffer with a buffer contacting each end of the gel,
a buffer shaper configured to be positioned near said gel support and in contact with the buffer, wherein said buffer shaper is positioned nearer to one portion of the gel support than to another portion of said gel support to cause the depth of buffer between said gel support and said buffer shaper to vary along the length or width of said gel support and buffer shaper wherein said apparatus comprises at least two electrodes, wherein said apparatus is configured and arranged to allow an electric current to pass along the length of the gel support and through the gel, and
a buffer and materials suitable for forming said gel.

* * * * *